United States Patent [19]
Keady

[11] Patent Number: 4,790,650
[45] Date of Patent: Dec. 13, 1988

[54] CONDENSATION NUCLEUS COUNTER
[75] Inventor: Patricia B. Keady, Minneapolis, Minn.
[73] Assignee: TSI Incorporated, St. Paul, Minn.
[21] Appl. No.: 40,540
[22] Filed: Apr. 17, 1987
[51] Int. Cl.$^4$ .............. G01N 31/00; G01N 1/00; G01N 15/02
[52] U.S. Cl. .................... 356/37; 356/337; 73/28; 377/10
[58] Field of Search ................ 356/37; 73/28
[56] References Cited
U.S. PATENT DOCUMENTS
3,694,085  9/1972  Rich ..................... 356/37
3,806,248  4/1974  Sinclair ................. 356/37
4,449,816  5/1984  Kohsaka et al. .......... 356/37

Primary Examiner—John S. Heyman
Attorney, Agent, or Firm—Merchant, Gould, Smith, Edell, Welter & Schmidt

[57] ABSTRACT

A condensation nucleus counter (1) for measuring particulate concentration within a gaseous environment, including an inlet orifice (3) leading to a flow path (5) within saturator (4). The resultant vapor (10) enters a condenser section (11) wherein the particulate matter suspended within serves as the nucleus for condensation. The enlarged droplets (23) thus formed enter a conventional optical particle counter section (15).

13 Claims, 2 Drawing Sheets

CONDENSATION NUCLEUS COUNTER

BACKGROUND OF THE INVENTION

1. Field of the Invention

The present invention relates generally to devices for counting the number concentration of fine particles suspended in air or gas, and, more particularly, pertains to that class of devices termed condensation nucleus counters. The primary purpose of the device is for monitoring air quality within designated areas, but it is useful in a variety of other scientific and industrial applications for counting the number of particles in the atmosphere.

2. Discussion of Related Technology

With the line widths of semiconductor devices going below 1 micrometer and the layer thickness below 0.1 micrometers, there is an increasing need for detecting and controlling submicrometer particles in the clean areas where the devices are manufactured. Particle contaminants much smaller than the line geometries can destroy the device and reduce production yield.

A common technique for detecting airborne particles is with an optical particle counter. Sample air flows into the device and intersects with a controlled beam of light. The particles in the sample air scatter the light in proportion to their size, shape and refractive index. The scattered light is collected onto a photoelectric device and converted into an electrical signal. The electrical signal is typically calibrated and processed to give the size distribution and number concentration of the particles. The theoretical lower limit of detection is approximately 0.05 micrometers diameter. Knollenberg R. G. and R. Luehr: Open Cavity Laser "Active" Scattering Particle Spectrometry, *Fine Particles*, edited by B. Y. H. Liu, Academic Press, Inc., New York (1976) pp. 669-696. The practical lower limit is closer to 0.1 micrometers diameter.

Another technique, useful for identifying and counting extremely small particles, is condensation nucleus counting. In this method, a liquid condenses on the particle, thus enlarging the target and thereby simplifying its identification. The theoretical lower limit of detection for a condensation nucleus counter is about 0.003 micrometers. Stolzenburg, M. R. and P. H. McMurry: Counting Efficiency of an Ultrafine Aerosol Condensation Nucleus Counter: Theory and Experiment, *Aerosols:Formation and Reactivity*, 2nd Int. Conf. Berlin, Pergamon Journals Ltd., Oxford, Great Britain (1986) pp. 786-789.

The literature describes three basic techniques for condensing vapor onto small particles for use in a counting instrument: (1) adiabatic expansion, (2) diffusional thermal cooling, and (3) two-flow mixing.

The first condensation technique (Aitken, J.: On the Number of Dust Particles in the Atmosphere. Proc. Royal Soc. Edinburgh, 35 (1888) uses adiabatic expansion of a water-saturated air-sample to cool and condense water onto small particles. In the Aitken method, the droplets are counted as they fall onto a grid. Later improvements to the technique include using light and electrical photodetectors to measure the light attenuation from the cloud formation, use of both under and overpressure systems, and automation of the flow system and adiabatic expansion. All of the presently available commercial instruments use water as the condensing fluid and operate in a pulsed flow fashion. The lowest particle concentration sensitivity obtainable with this method is approximately 100 particles/cm$^3$.

The second condensation technique (Madelaine and Reiss, United Kingdom Pat. No. 1,422,188 and Sinclair, U.S. Pat. No. 3,806,248) utilizes continuous-flow thermal-diffusional cooling of an alcohol vapor. The air sample is saturated with alcohol vapor as it passes over a heated pool of liquid alcohol. The vapor-aerosol mixture is then cooled by thermal diffusion from the cold walls of the condenser tube. The vapor supersaturates and condenses on the surface of the particles so as to form larger droplets. The droplets are detected in a conventional optical particle detector or by photo attenuation of a light beam. A commercial instrument (Agarwal, J. K. and G. J. Sem: Continuous Flow, Single-Particle-Counting Condensation Nucleus Counter. J. Aerosol Sci., Vol. 11, No. 4, (1980) pp. 343-357) employs two modes of concentration measurement to cover the range of particle concentrations from 0.01 to 10$^7$ particles/cm$^3$. For particle concentrations of less than 1000 particles/cm$^3$, the optical detector counts individual particle-produced pulses as they pass individually and sequentially through the beam of light. For higher particle concentrations, the total amount of light scattered, measured as the DC electrical signal from the photodetector, is calibrated to a known concentration using the electrical calibration technique (Liu, B. Y. H. and D. Y. H. Pui: A Submicron Aerosol Standard and the Primary Absolute Calibration of the Condensation Nucleus Counter. J. Colloid Int. Sci., Vol. 47 (1974) pp. 155-171).

The third condensation technique (Kohsaka, Nonaka, and Tachibana, U.S. Pat. No. 4,449,816) turbulently mixes two aerosol-laden vapors, one hot and one cool, which causes rapid vapor supersaturation and condensation on the particles. The droplets are counted with a conventional optical particle detector. The two flows are continuous. The concentration range is similar to the previously discussed diffusional-cooling technique.

The present invention, a condensation nucleus counter, is a device that detects and counts the number concentration of small airborne particles predominantly in the submicrometer size range.

The device is not limited to air, but is suitable for many other gases as well. Condensation formed on the particles from a supersaturated vapor enlarges the particle size and forms liquid droplets. The droplets are detected with a light scattering technique similar to that used in an optical particle counter. The lower detection limit of the present invention is a particle of approximately 0.014 micrometer diameter. The invention uses a similar principle of operation to the continuous-flow thermal-diffusional technique. The unique features of this invention have improved the performance, reduced the size, increased reliability, stability, and ruggedness, and provide for contamination-free operation in clean environments.

SUMMARY OF THE INVENTION

The present invention is an instrument that continuously counts the number concentration of submicrometer particles from concentrations of zero to $5 \times 10^4$ particles/cm$^3$ and has design features that make it small, rugged, reliable, noncontaminating, and otherwise compatible with the clean environment.

DETAILED DESCRIPTION OF THE INVENTION

Figure 1:
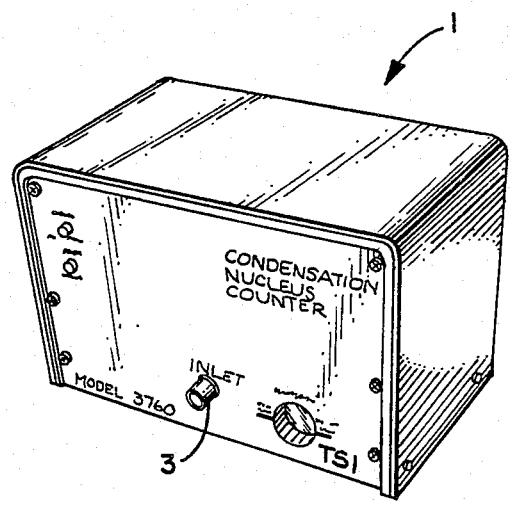
FIG. 1 is a perspective view of a preferred embodiment of an apparatus constructed according to the principles of the present invention.
Figure 2:
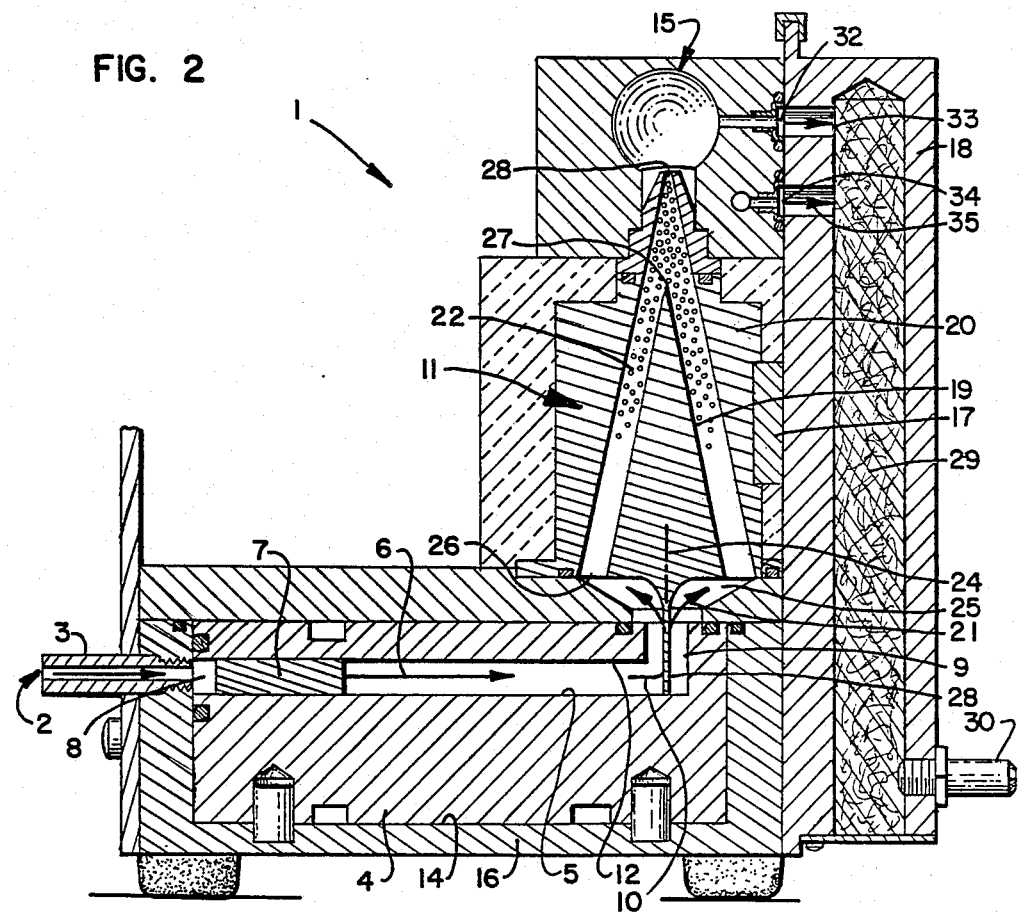
FIG. 2 is an elevation in section, showing particularly the saturator and reservoir section.

As seen in FIGS. 1 and 2, the apparatus 1 constructed according to the principles of the present invention is compact in design and its many elements interact with each other to make an efficient and reliable particle concentration measurement instrument.

Figure 3:
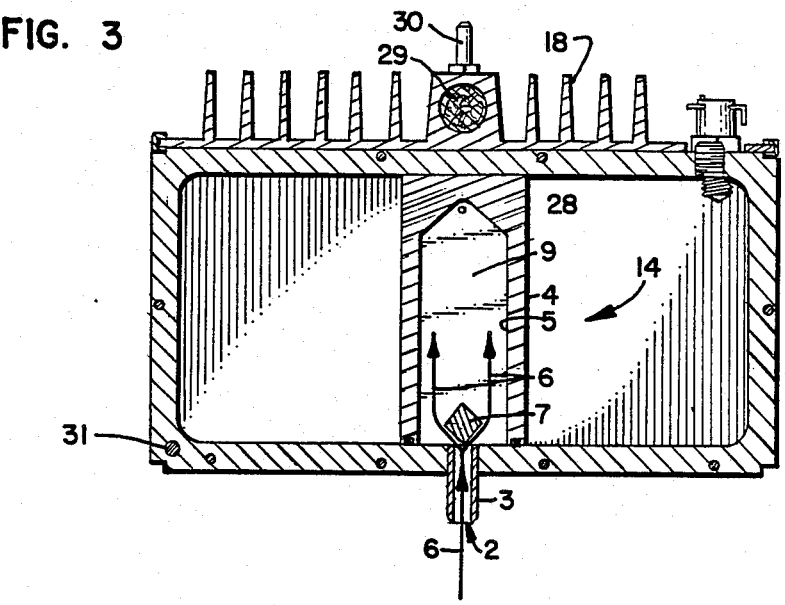
FIG. 3 is a plan in section of the saturator of the apparatus depicted in FIG. 1.

As best seen in FIGS. 2 and 3, the sample gas 2 enters the inlet tube 3 of the instrument 1, the inlet tube 3 leading to saturation chamber 4. The saturation chamber 4 is formed from a block of electrically conductive porous material such as fused polyethylene beads impregnated with carbon black. Formed integrally within the saturation chamber 4 is a slotted-hole flow path 5 through which the sample gas 2 passes. The saturator block 4 constitutes a liquid reservoir 14 and continuously wicks the condensing fluid (not shown) to the gas stream 6. The liquid evaporates and nearly saturates the gas 6 as it passes through slotted hole flow path 5. A solid, electrically conductive flow deflection piece 7 at the entrance 8 to the saturation chamber 4 forces the gas 2 to flow more uniformly through the entire width of the flow slot 5. At the exit 9 of the saturation chamber, the flow path is constricted and turned 90 degrees so as to evenly mix the vapor-particle stream 10 before the stream 10 enters the condenser section 11.

The saturator block 4 is constructed so as to be electrically conductive in order to avoid the accumulation of a static electrical charge and the subsequent attraction and deposition of aerosol particles on the walls 12 of the flow slot 5.

The flow path 5 is formed so as to have a slotted, high aspect ratio rectangular cross-section in order to increase the exposed surface area of the porous walls for a given volume and, thereby, enhance the evaporation process. A high surface area has the advantage of decreasing the residence time required of the gas stream 2 in the region adjacent to the saturator block 4, and also permits a shorter length for flow path 5, thereby permitting the construction of a more compact, portable apparatus. In a preferred embodiment of the present invention, the height of flow path 5 is approximately 0.2" and the width is approximatley 1". Previous nucleus condensation counter designs have used a circular saturator flow path.

The porous block material 4 acts much like a sponge and tends to completely absorb all of the liquid in which it is immersed before becoming unusable due to excessive drying. This novel feature provides maximum durational use of the instrument before there is a need to add more liquid (not shown) to the reservoir 14. Also note that liquid draining and filling goes through fitting 32 as shown in FIG. 3. This feature also allows the instrument to be filled with liquid and subsequently drained and still have ample liquid in the block 4 for several hours of accurate operation. This is useful for operation in airplanes and other dynamic applications where the instrument may be tipped or operated in other than an upright fashion for extended time periods.

The gas flow path 5 and the liquid reservoir 14 are isolated from each other by the porous block material 4. The liquid (not shown) permeates throughout the block creating a continuous leak-free seal for the sample gas 6 in the flow path 5. The instrument 1 can be tipped momentarily in any direction and the flow of liquid (not shown) will be impeded. The likelihood of liquid spilling out of the instrument or into the condenser 11 and optics section 15 is reduced. The instrument 1 may be easily transported without having to first drain the reservoir 14.

The reservoir 14 is formed integrally within the entire base 16 of the instrument. The base/reservoir provides structural strength and acts as an additional heatsink for the dissipation of heat from the thermoelectric device 17 used in the condenser section 11. The reservoir 14 is in physical and thermal contact with the back panel heatsink 18. The operating temperature of the section formed by the reservoir 14 and saturator 4 is typically a few degrees above ambient temperature. The reservoir 14 temperature is not controlled to a specific value and no additional heat is added by means of an electrical heater. The temperature of the reservoir is monitored by sensor 31, and used to control the temperature of the condenser by means of electrical circuitry well known in the art.

The vapor-aerosol stream 6 flows past saturator 4 via slotted flow path 5 and into the condenser section 11. The condenser 11 is cooled by means of a thermoelectric heat pump 17 that is sandwiched between the condenser block 20 and a heatsink 18. The condenser block 20 is thermally insulated from the rest of the instrument 1. The vapor 21 is cooled by thermal diffusion from the cold walls 19 of the condenser 11. The vapor 21 supersaturates and condenses on the particles (not visible) and on the condenser walls 19. The condenser 11 is oriented vertically so that liquid that condenses on the walls 19 will run back down into the saturator section 4. The vapor that condenses on the particles forms droplets 22 that will be detected optically with a single-particle-counting optical-detector 15 as is well known in the art. Particles are generally not visible, although droplets may be. The droplets 22 increase in size as they travel upwardly within the condenser 11.

As the gas stream 10 enters the condenser section 11, the flow 21 is equally divided into multiple flow paths. The condenser 11 comprises a plurality of entrance zones 26 that are equally spaced on a radius about the centerline 24 at the condenser entrance 25. The zones 26 are aligned laterally, the longitudinal axes of the flow paths 21 thus defined thereby forming an acute angle near the top 27 of the condenser 11. The multiple flow paths 21 combine at the top 27 of the condenser and flow through a nozzle 28 into the optical section 15.

The size of the particle 22 that can act as a nucleus site for condensation depends on the supersaturation level of the condensing fluid and absolute temperature. Smaller particles will require a higher level of supersaturation for condensation than a larger particle will. The supersaturation profile in the condenser passages 26 depends on the flow rate, condensing fluid properties, gas properties, incoming gas temperature, and the temperature of the condenser wall. The maximum supersaturation level will occur at some distance from the entrance of the hole 25. Beyond the point of maximum supersaturation, no new particles will be activated as condensation sites. Particles that were too small to be activated will remain as ultrafine particles and will not be detected in the optical system 15. The remaining length of the condenser beyond the maximum supersaturation point is used for continued condensation and droplet growth.

Reducing the flow rate in the condenser passages will cause the maximum supersaturation level to occur at a shorter distance from the condenser entrance 25. Similarly, higher flow rates will cause the maximum supersaturation level to occur further from the condenser entrance. The absolute value of the maximum supersaturation does not change appreciably with flow rate. By using multiple flow paths in the condenser 11, the overall flow rate of the instrument can be increased without needing to increase the length of the condenser tube. The flow rate increase is an integral factor equal to the number of separate flow paths in the condenser. This invention uses multiple flow paths in the condenser and is, therefore, much smaller than previous designs and also has a higher sampling flow rate. The preferred embodiment of the present invention comprises 8 flow paths having a typical flow capacity of 0.177 L/min each, resulting in a total flow of 1.415 L/min.

A small wire rod 28 is connected at the center 24 of the condenser 11 at its entrance 25 and extends down and touches the saturator block 4. Liquid that runs down the rod into the saturator 4 without dripping. Drips would cause small particles to be released in the sample flow and result in false detection of particles. The condenser has a smooth, rounded point where the rod is connected. This has a twofold purpose: (1) so that liquid drops will not accumulate on the condenser but will continuously and smoothly flow down the rod, and (2) so the gas flow will be evenly divided between the condenser holes.

The temperature of the condenser is measured and compared to the temperature of the reservoir. The temperature sensors 31 are resistance thermistors. The temperature of the condenser is controlled to maintain a constant thermistor resistance ratio. The electrical output to the thermoelectric heat pump 17 is adjusted until the condenser block registers the correct temperature to maintain this ratio. Because the thermistors are not absolutely linear, the electrical circuit does not maintain a constant temperature differential between the saturator reservoir and condenser.

Ideally, the instrument has the same detection efficiency for small particles under all operating conditions. In other words, the smallest particle that could be activated for condensation would be the same for all ambient operating temperatures. Vapor supersaturation is not constant with a constant temperature differential between the condenser and saturator if the absolute temperature changes. At higher absolute temperature, a larger temperature differential is required to maintain the same supersaturation level. By using the resistance ratio of the thermistors to control the condenser temperature, the temperature differential does increase with increasing absolute temperature. In the preferred embodiment of the present invention, the maximum supersaturation and minimum detectable particle size varies over only a relatively small range throughout the ambient operating temperature range of 10 to 45 degrees Celsius.

The sample flow exits the condenser 11 through a plastic nozzle 28 into the optical detector 15. The single-particle-counting optical detector uses a solid state 3 mW laser diode for the light source. The laser light is collimated and focused with a cylindrical lens into a very thin sheet of light just above the nozzle tip. The droplets exiting the nozzle scatter the laser light. The combination of the high velocity of the droplets as they exit the nozzle and the narrow focused laser viewing volume results in a pulse of scattered light that is only about 0.25 microseconds in duration. The scattered light is collected in a near forward scatter direction and focused onto a photodetector. The photodetector transforms the light into an electrical signal. The main beam of laser light is stopped with a light stop.

The minimum electrical pulse height is approximately 200 mV, and electrical noise is about 10 mV, giving a signal-to-noise ratio of greater than 20 to 1. Since all of the droplets grow to nearly the same size, every particle produces a signal pulse well above the electronic noise level. The counting trigger is set to about 60 mV, also well above the noise level.

The large signal-to-noise ratio virtually eliminates the possibility of false counting due to electrical noise. The instrument is accurate for low particle concentration measurement. Many hours of measurements can be made of absolutely particle-free air without a single count being registered. Accurately measuring aerosols with very low concentration is of particular importance to the microelectronics and pharmaceutical industries and other applications needing ultra-clean air or gas.

The instrument is also capable of measuring relatively high concentrations accurately while still counting single particles. The coincidence error at high concentrations is the counting error due to more than one particle being in the viewing volume at the same time, such that only one count is registered for the multiple particles. Coincidence is calculated by the following equation:

$$N_a = N_i \exp(N_a Q t)$$

where
$N_a$ = actual concentration
$N_i$ = indicated concentration
$Q$ = sample flow rate
$t$ = effective time each particle spends in the viewing volume.

For $t = 0.25$ microseconds (pulse width) and $Q = 1.4$ L/min, the coincidence error for $10^4$ particles/cm$^3$ is only 6%. This is a great improvement over previous designs of condensation nucleus counters and optical particle counters.

The wide dynamic concentration range is useful for measuring the quality of filters. The instrument can measure both the upstream and downstream side of a filter without the necessity of dilution or modification to the sample. Other applications for the high concentration measurement is for general aerosol research, atmospheric sampling, remote sampling, and submicrometer size distribution measurement using ancillary devices such as a differential mobility analyser, diffusion battery, or electrical aerosol analyzer.

The optical housing 15 is in physical and thermal contact with the heatsink 18 and is several degrees above ambient temperature. Once the droplets leave the cold condenser 11, the liquid starts to evaporate as the gas stream warms. Liquids with a high vapor pressure, such as isopropyl or n-butyl alcohol, will evaporate very quickly. The droplets are large when passed through the laser viewing volume, but they soon evaporate completely leaving only the original particle. Particles that recirculate in the optics housing from flow eddies are too small to scatter much light as they float through the laser beam. Recirculating particles will not affect the accuracy of the particle concentration measurement. The heated optical housing ensures that the working fluid will vaporize and will not collect to form a liquid pool in the optics that could affect the detection capabilities.

From the optics 15, the gas flow passes through a critical orifice 32 made of sapphire and out to an external vacuum source. The orifice controls the flow at a constant flow rate no matter what the vacuum pressure, provided the ratio of downstream to upstream pressure is at least 0.528. The size of orifice 32 and the optics nozzle 28 together restrict the flow to the desired flow rate. Pressure variations at the inlet of the instrument will change the flow rate some, and can be corrected in the final concentration calculations.

The critical orifice 32 is positioned in the optical housing 15. The flow through the orifice continues through a passage 33 in the spine of the heatsink 18. The cooler sample gas helps to cool the heatsink. The connector port 30 for the vacuum flow source is located at the base of the heatsink 18. The vacuum flow passage in the heatsink is filled with copper mesh 29 to increase the heat transfer from the heatsink 18 to the gas.

The entire flow path from the inlet of the instrument to the optical sensing volume is short and streamlined. The possibility of flow eddies is minimized. In the preferred embodiment of the present invention, the calculated flow transit time through the instrument for 1.4 L/min is less than one second. The measured response time of the instrument, which accounts for small flow eddies, is also very low. The response to a step change in aerosol concentration is about 2 seconds, even when going from high to low concentration. The fast response time is important when measuring rapidly changing aerosol conditions; for example, aircraft studies, air-pollution studies, smokestack plumes, filter scanning systems, and clean-area monitoring.

The heatsink 18 makes up the entire back panel of the instrument and is exposed to the ambient air. It dissipates heat by natural convection to the surrounding air. Some of the heat is dissipated to the connecting parts of the instrument and to the gas stream, as already described. The instrument does not use a cooling fan, thus avoiding the generation of contaminating particles in the clean environment. The instrument avoids moving mechanical devices which can produce particles by friction and heat. The instrument is designed to be clean and is especially useful for ultra-clean areas.

A second parallel critical orifice 34 connected to the "vacuum" tube in the heatsink controls the flow of purge air from inside of the instrument cabinet 1. The purge air 35 and sample gas 2 mix inside of the vacuum tube and together exit the instrument out to the vacuum source. The purge air has two purposes: (1) the continuous purging of the air from within the cabinet helps to cool the internal electronics and mechanical parts, further reducing the need for cooling fans, and (2) if particles are generated within the cabinet, possibly from combustion or evaporation and condensation around hot electrical devices, they are quickly swept away through the vacuum line and cannot escape into the surrounding air and cause contamination. The slight underpressure inside the cabinet causes particles and air to leak into the cabinet—not out.

EXAMPLE INSTRUMENT

An example of the above-described instrument was constructed and operates with a sample flow rate of 1.415 L/min. The purge flow is also 1.4 L/min. The saturator block is made from a molded, carbon-impregnated, polypropylene, porous material. The condensing fluid is typically n-butyl alcohol or isopropyl alcohol. The reservoir holds up to 210 ml of liquid. At an ambient temperature of approximately 25° C., the instrument will operate continuously for up to 4 days without needing to refill the reservoir with more alcohol. The reservoir, condenser, optical housing and heatsink are made from anodized aluminum. The condenser comprises eight flow passages with inside diameters of 0.186 inches and a length of 2 inches. The operating temperatures of the reservoir and condenser are typically 28° C. and 8° C. respectively at an ambient temperature of 25° C. The smallest sized particle that can be detected (50% detection efficiency) is 0.014 micrometers. The overall size of the instrument is 140 mm×155 mm×220 mm and the weight is just under 4 kg.

I claim:

1. A thermal-diffusional continuous-flow condensation nucleus counter comprising:
   (a) a reservoir;
   (b) a saturator block, the saturator block residing within the reservoir, the saturator block being formed of a porous, electrically conductive material such that a static electric charge cannot be accumulated in regions in fluid communication with the reservoir;
   (c) a liquid, the liquid being housed within the reservoir, the liquid thereby permeating throughout the saturator block;
   (d) a sample gas stream, the sample gas stream being in fluid communication with the reservoir, the reservoir having a volume substantially filled by the saturator block, the sample gas thereby entraining the vapor from the saturator block;
   (e) a cooling condenser, the condenser substantially surrounding the sample gas stream as the sample gas exits the reservoir, the condenser serving to cool the sample gas stream such that the entrained vapor condenses on any particulate matter residing within the sample gas stream so as to form droplets relatively larger than the particulate matter; and
   (f) indicating means, the indicating means encountering the sample gas stream as the sample gas stream exits the cooling condenser, the indicating means serving to count and identify the number of droplets formed within the sample gas stream.

2. The condensation nucleus counter of claim 1 wherein the liquid residing in the reservoir is an alcohol.

3. The condensation nucleus counter of claim 2 wherein the sample gas stream is introduced into a region proximate the saturator block via a flow passage, the flow passage having a slotted cross section configured so as to optimize the exposed surface area of the gas stream to the saturator block, thereby enhancing evaporation of the liquid into the sample gas stream.

4. The condensation nucleus counter of claim 3 wherein the cooling condenser comprises a plurality of flow passages, thereby permitting an increased flow rate through a relatively compact condenser.

5. The condensation nucleus counter of claim 4 wherein the plurality of flow passages within the condenser are formed as at least one pair of two convergent flow passages, each flow passage having an entrance end and an exit end, each entrance end being adjacent to the saturator block so as to receive the sample gas stream, the exit end of each flow path converging to a common region, the common region leading to an area in which the indicating means may process the sample gas stream.

6. The condensation nucleus counter of claim 5 wherein the flow passages within the condenser are oriented in a substantially vertical position.

7. The condensation nucleus counter of claim 5 wherein each pair of flow passages is formed so as to create a front flow passage and rear flow passage, each flow passage having a longitudinal axis, each longitudinal passage being displaced at approximately the same angle from a perpendicular plane, the exit end of each flow passage meeting at a common apex region.

8. The condensation nucleus counter of claim 7 further comprising a rod, the rod being formed integrally with the condenser, the rod being located within the perpendicular plane about which each flow passage is equally angularly displaced, the rod extending from the condenser to the saturator so as to allow liquid that has condensed within the cooling condenser to flow into the saturator as a continuous stream.

9. The condensation nucleus counter of claim 8 further comprising temperature control means. The temperature control means controlling the temperature of the condenser in relation to the temperature of the reservoir such that a desired supersaturation ratio may be maintained.

10. The condensation nucleus counter of claim 9 wherein the indicating means comprises a heated optical housing, the heated optical housing serving to evaporate liquid droplets after the droplets have been detected and counted within a desired viewing volume.

11. The condensation nucleus counter of claim 10 further including heat dissipating means, the heat dissipating means comprising an airflow passage which receives the sample gas stream after the sample gas stream has exited the heated optical housing, the airflow passage being filled with a thermally-conducting mesh mounted within a heatsink.

12. The condensation nucleus counter of claim 11 further comprising evacuation means, the evacuation means tending to remove gas from inside the instrument cabinet, secondary to the sample gas, to remove airborne contaminants from within the cabinet.

13. A method of measuring particulate matter concentration within sample gas streams, comprising the steps of:
(a) saturating a block formed from a porous material with a volatile liquid;
(b) introducing the sample gas stream through a slotted cross section flow passage, the flow passage being in fluid communication with the saturator block such that the liquid may readily evaporate within the sample gas stream;
(c) routing the resultant sample gas stream through a condenser section, the condenser section being formed from a plurality of air flow passages, the flow passages being configured as a front flow passage and a rear flow passage, each flow passage being equally angularly displaced about a perpendicular plane such that particulate matter within the gas stream will serve as a nucleus for condensation, thereby forming a droplet corresponding to each discrete particle;
(d) passing the resultant sample gas stream through an optical counter in order that the droplets may be identified and counted; and
(f) heating the sample gas stream exiting from the optical counter so as to cause the evaporation of the droplets, thereby preventing the counting of a particular droplet more than once.

* * * * *